United States Patent [19]

Nielsen et al.

[11] Patent Number: 5,278,593
[45] Date of Patent: Jan. 11, 1994

[54] OPHTHALMIC DIAL ADVANCEMENT SYSTEM

[75] Inventors: Ronald R. Nielsen, Oak Park; Erwin Witt, Arlington Heights, both of Ill.

[73] Assignee: Woodlyn, Inc., Arlington Heights, Ill.

[21] Appl. No.: 853,486

[22] Filed: Mar. 18, 1992

[51] Int. Cl.$^5$ ................................. A61B 3/02
[52] U.S. Cl. ........................... 351/235; 351/234
[58] Field of Search .......... 351/234, 235, 233, 216, 351/217, 229, 240, 222, 245

[56] References Cited

U.S. PATENT DOCUMENTS

| | | | |
|---|---|---|---|
| 1,240,289 | 9/1917 | Woolf | 351/234 |
| 2,322,878 | 6/1943 | Peck et al. | 351/235 |
| 2,923,200 | 2/1960 | Wright | 351/235 |
| 2,949,810 | 8/1960 | Wright | 351/235 |
| 2,968,213 | 1/1961 | Wright et al. | 351/235 |
| 3,498,699 | 3/1970 | Wilkinson | 351/235 |
| 4,523,822 | 6/1985 | Thurston | 351/234 |
| 4,798,457 | 1/1989 | Morohashi et al. | 351/235 |

FOREIGN PATENT DOCUMENTS 598683 5/1960 Canada .................. 351/235

Primary Examiner—Bruce Y. Arnold
Assistant Examiner—David R. Parsons
Attorney, Agent, or Firm—Dick and Harris

[57] ABSTRACT

An ophthalmic dial advancement system for vision testing apparatuses, such as ophthalmic refractors of the type which utilize a single dial sphere control for advancing the lens power of at least one of the lenses positioned within the lens housing. A rotation element is positioned adjacent a portion of the engagement surface of the single dial sphere control so as to facilitate a controlled and sensitive advancement of the single dial sphere control and, in turn, the lenses which are being rotated thereby. A rotation disengagement member is operably attached to a portion of the lens rotation element so as to enable alternatively engaged and disengaged advancement of the single dial sphere control. In addition, barrier pieces are integrally attached to the lens housing of the vision testing apparatus so as to shield the adjustment knobs and dials, and, more particularly, the single dial sphere control positioned thereon, from a patient's hands during an ophthalmic examination, as well as to facilitate manipulation of one or both of the sphere dial and lens rotation elements by the practitioner.

16 Claims, 3 Drawing Sheets

OPHTHALMIC DIAL ADVANCEMENT SYSTEM

BACKGROUND OF THE INVENTION

The present invention relates in general to lens advancement devices, and, more particularly, to an ophthalmic dial advancement system for vision testing apparatuses, such as an ophthalmic refractor of the type which utilizes a single dial sphere control for advancing the lens power of at least one of the lenses positioned within the lens housing of the ophthalmic refractor.

Traditionally, vision testing apparatuses, and, more particularly, ophthalmic refractors, have utilized a single dial sphere control, or "diopter dial," for advancement of the lenses within the apparatus housing in ¼ diopter steps. Accordingly, one complete rotation of the diopter dial would advance the lens through four different diopter powers—wherein one diopter power focuses on an image at a distance of one meter; a two diopter power focuses on an image at a distance of one half of a meter, etc. Such advancement of the diopter dial, and in turn, the diopter power, is necessary to determine the strength of the corrective eye lenses which a patient will need.

Actual advancement of the diopter power is effectuated by the practitioner directly advancing the diopter dial with his or her hand until he or she actually "feels" the lenses within the refractor properly advance to the next ¼ diopter step. Such a "feel" is achieved by slight resistance imparted to the diopter dial. Unfortunately, inasmuch as diopter dials are generally engineered for smooth and easy advancement, it is not uncommon for a practitioner to inadvertently advance the diopter dial past the next intended diopter step—thus causing additional manipulation of the diopter dial, and, quite possibly, an incorrect diagnosis of the patient's vision.

Although such prior art vision testing apparatuses do offer the advantage of a single dial sphere control (diopter dial) for the advancement of the diopter power, few, if any, have provided a separate lens rotation member which not only reduces the likelihood of excessive advancement of the diopter dial during advancement of the diopter power, but which also imparts increased sensitivity to the practitioner's hands during such advancement—thereby substantially reducing inadvertent under and/or over rotation of the diopter dial with respect to the desired diopter power. Furthermore, few, if any of such prior art has provided such a cooperating lens rotation member which is alternatively positionable between a first engaged position and a second disengaged position with respect to the diopter dial, for alternative advancement of the diopter dial directly or indirectly, with or without the cooperating lens rotation member being engaged therewith respectively.

Additionally, inasmuch as prior art ophthalmic refractors have their adjustment dials and knobs positioned on or partially exposed to the surface of the lens housing which is adjacent to the practitioner during an eye examination, it is not uncommon for the patient to inadvertently, or through curiosity, place his or her hands on the testing equipment, and in turn, on one or more of the adjustment dials and knobs. Inasmuch as the diopter dial has its advancement portion positioned adjacent to the outer peripheral side surface of the lens housing, it is this critical adjustment dial which a patient's hands would most likely contact—thereby potentially moving the diopter dial and, in turn, inadvertently altering the diopter step. Although a patient's inadvertencies and/or curiosities with respect to touching the adjustment mechanisms, and, more particularly, the diopter dial, cannot be totally curtailed, few, if any prior art vision testing apparatuses teach, much less disclose, a barrier member which shields exposure of the diopter dial to a patient, while at the same time serving as a guide for utilization of the present dial advancement system, as a function of the practitioner's manipulation during the examination procedure.

It is thus an object of the present invention to provide an ophthalmic dial advancement system which provides a barrier member attached to a vision testing apparatus which helps reduce inadvertent, or curiosity, contact by a patient with the adjustment mechanisms, and more particularly, the diopter dial, on the lens housing, as well as which can serve as a hand guide for the practitioner utilizing the lens rotation member or, when directly advancing the diopter dial.

It is further an object of the present invention to provide an ophthalmic dial advancement system which includes an integrateable lens rotation member for facilitating indirect and more precise and sensitive advancement of the diopter dial, and, in turn, the diopter steps.

It is also an object of the present invention to provide an ophthalmic dial advancement system which includes a lens rotation member which is alternatively positionable between a first engaged rotational position, with respect to the diopter dial, and a second disengaged rotational position.

It is still further an object of the present invention to provide an ophthalmic dial advancement system wherein the diopter dial can be alternatively advanced directly regardless of engagement or disengagement relative to the lens rotation member.

These and other objects of the present invention will become apparent in light of the present specification and drawings.

SUMMARY OF THE INVENTION

The present invention comprises an ophthalmic dial advancement system for vision testing apparatuses, such as an ophthalmic refractor of the type having symmetrically configured lens housing means wherein each of the lens housing means include a front side and a back side, an outer peripheral side edge and a plurality of adjustment knobs and dials, including a single dial sphere control having an outer engagement surface operably exposed adjacently to at least one of the first and second sides of each of the lens housing means for advancing the lens power of at least one of the lenses in each of the lens housing means.

The ophthalmic dial advancement system includes lens rotation means operably positioned adjacent to at least one of the front sides and back sides of the lens housing means in operable contact with the engagement surface of the single dial sphere control for facilitating the alternative advancement of the single dial sphere control upon turning of the lens rotation means. Accordingly, the lens rotation means provides increased manual sensitivity to a practitioner during the advancement of the single dial sphere control to, in turn, preclude inadvertent under or over advancement of the desired lens power.

The lens rotation means has a top surface, a bottom surface, an outer peripheral surface and a shaft member. The shaft member has a shaft region operably attached to at least one of the top and bottom surfaces of the lens rotation means, and a bottom end attached adjacent to at least a portion of the lens housing means. The lens rotation means further includes engagement means operably positioned along at least a portion of one or more of the top surface, bottom surface and/or outer peripheral surface of the lens rotation means, for facilitating operable contact, and, in turn, rotational advancement of the single dial sphere control upon turning of the lens rotation means by the practitioner. When operably aligned, the engagement means contacts and engages at least a portion of the outer engagement surface of the single dial sphere control to impart rotation thereto, upon rotational advancement of the lens rotation means.

In a preferred embodiment of the invention, the ophthalmic dial advancement system further includes rotation disengagement means which are operably attached to the lens rotation means for facilitating manipulatable positioning of the lens rotation means between a first engaged rotational position and a second disengaged rotational position. Such manipulatable positioning enables alternative engaged and disengaged rotational advancement of the single dial sphere control as a function of rotation of the lens rotation means.

The rotation disengagement means includes engagement locking means which are operably associated with at least a portion of the lens rotation means for releasably maintaining the lens rotation means in either its first engaged rotational position, or its second disengaged rotational position. Furthermore, the locking means include retaining means which are operably positioned within a portion of the lens housing means for releasable engagement with a portion of the shaft member.

In this preferred embodiment of the invention, the retaining means includes channel means for operable acceptance of a portion of the shaft member of the lens rotation means. The portion of the shaft member which is to be accepted within the channel means includes one or more grooved sections. Furthermore, the channel means includes one or more protrusions which operably extend into a portion of the channel means and are intended to cooperate with the grooves on the shaft member for releasable securement of the lens rotation means in either the first engaged rotational position or the second disengaged rotational position.

In a preferred embodiment of the invention, the one or more protrusions include biasing means for insertion and release of the one or more protrusions within the one or more grooves of the shaft member during positioning of the lens rotation means between the first engaged rotational position or the second disengaged rotational position.

In another embodiment of the preferred invention, the shaft member of the lens rotation means is releasably secured within the channel means of the retaining means as a result of a snap-fit connection therebetween. Accordingly, the protrusions within the channel means could comprise rib members which do not bias.

In still another embodiment of the invention, at least a portion of the rotation disengagement means is operably disposed between the bottom surface of the lens rotation means and the lens housing means.

In a preferred embodiment of the invention, the engagement means comprises material having a relatively high coefficient of friction applied to at least a portion of the outer peripheral surface of the rotation means for providing frictional engagement with the outer engagement surface of the single dial sphere control upon turning of the lens rotation means.

In yet another preferred embodiment of the invention, the engagement means comprises a substantially elastomeric ring of material having a relatively high coefficient of friction operably attached to at least a portion of the outer surface of the lens rotation means. This elastomeric ring of material provides frictional engagement with the outer engagement surface of the single dial sphere control upon turning of the lens rotation means.

In another embodiment of the invention, the engagement means comprises a surface which is substantially engageable with the outer engagement surface of the single dial sphere control for communicating rotation thereto.

In the preferred embodiment of the invention the ophthalmic dial advancement system further includes barrier means which are operably attached to a portion of each of the two symmetrical lens housing means for restricting a patient from hand contact with at least one of the plurality of adjustment knobs and dials which are positioned on the lens housing means. Furthermore, these barrier means also serve to facilitate guided manipulation of the rotation means and, the single dial sphere control by a practitioner. The barrier means have a front panel, a back panel, an outer peripheral side panel disposed between the front and back panel, and an inner edge panel opposing the outer peripheral side panel, wherein the inner edge panel is operably attached contiguously with at least a portion of the outer peripheral side edge of the lens housing means.

The barrier means comprise extension pieces which are integrally formed with a portion of the outer peripheral side edge of the lens housing means. In addition, the lens rotation means are operably attached to a portion of the barrier means.

DETAILED DESCRIPTION OF THE DRAWINGS

Figure 1:
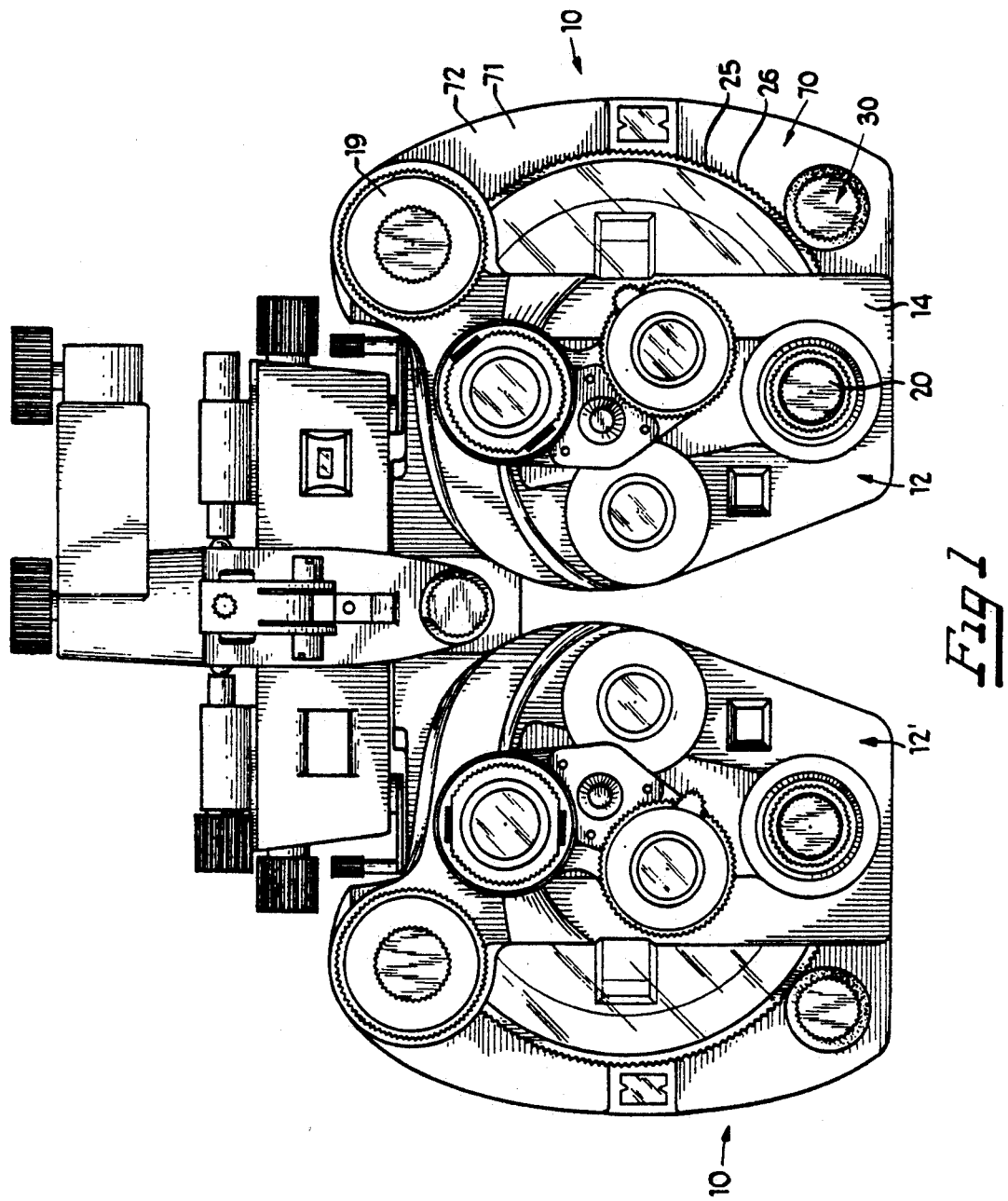
FIG. 1 of the drawings is an elevated front view of the ophthalmic dial advancement system as integrally attached to a prior art ophthalmic refractor, showing, in particular, the integrateable lens rotation means and the barrier means integrally attached to the lens housing of the ophthalmic refractor.

While this invention is susceptible of embodiment in many different forms, there is shown in the drawings and will herein be described in detail, several specific embodiments with the understanding that the present disclosure is to be considered as an exemplification of the principles of the invention and is not intended to limit the invention to the embodiments illustrated.

Figure 2:
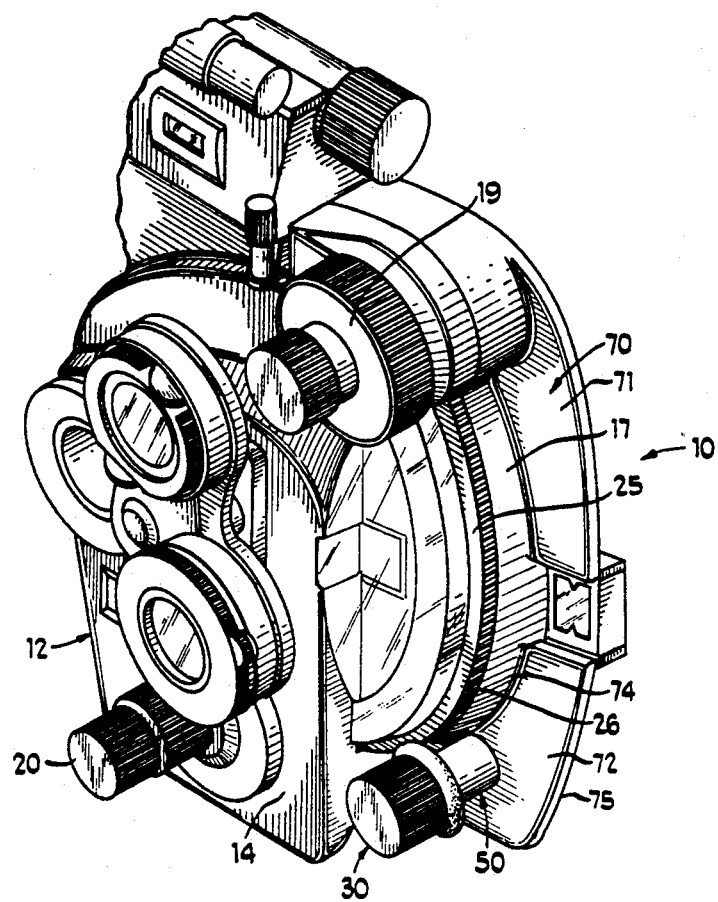
FIG. 2 of the drawings is a front perspective view of the ophthalmic dial advancement system as integrally attached to one of the housing means of the ophthalmic refractor as shown in FIG. 1, and, showing in particular, the engagement means of the integrateable lens rotation means adjacently positioned to the outer engagement surface of the single dial sphere control of the ophthalmic refractor.

Ophthalmic dial advancement system 10 is shown in FIG. 1 and FIG. 2 as being integrally attached to housing means 12 and 12' (which other than ophthalmic advancement system 10 comprises part of a prior art ophthalmic refractor). Housing means 12 and 12' are substantially identical to each other and therefore reference will be made only to housing means 12. Accordingly, housing means 12 includes front side 14, back side 15 (FIG. 3), outer peripheral side edge 17 (FIG. 2), a plurality of knobs, such as knobs 19 and 20 and single dial sphere control (diopter dial) 25 operably positioned adjacent front side 14 of housing means 12. In particular, single dial sphere control 25 includes outer engagement surface 26 which is operably exposed adjacent outer peripheral side edge 17 of lens housing means 12. Although not shown, single dial sphere control 25 is used to advance the diopter power of one or more of the lenses on and/or in the housing means.

Figure 4:
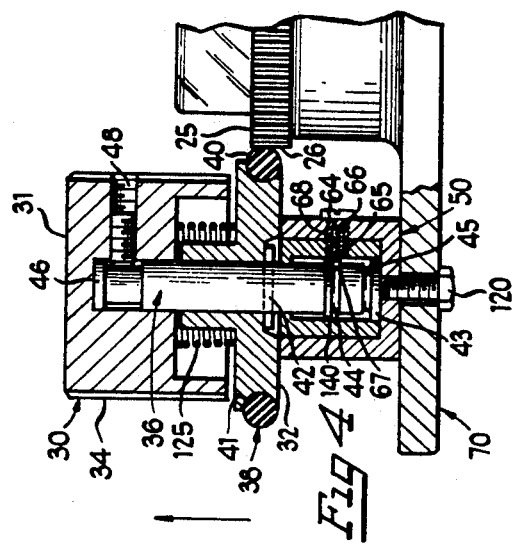
FIG. 4 of the drawings is an enlarged cross-sectional view of a portion of the ophthalmic dial advancement system showing, in particular, the lens rotation means including the rotation disengagement means, as attached to the barrier means, the shaft member of the lens rotation means, and, the engaged positioning of the engagement means of the integrateable lens rotation means with the outer engagement surface of the single dial sphere control of the ophthalmic refractor.

Ophthalmic dial advancement system 10 comprises lens rotation means 30, which includes rotation disengagement means 50 (FIG. 2), and barrier means 70. Lens rotation means, as shown in detail in FIG. 4 and FIG. 5, includes top surface 31, bottom surface 32, outer peripheral surface 34, shaft member 36 and engagement means 38 which is operably positioned along a portion of outer peripheral surface 34. Engagement means 38 comprises elastomeric ring of material 40 and groove portion 41 which facilitates operable seating of the elastomeric ring of material. Elastomeric ring of material 40 has a relatively high coefficient of friction so as to provide frictional engagement between engagement means 38 and outer engagement surface 26 of single dial sphere control 25 when lens rotation means is in its engaged rotational position, as shown in FIG. 4. Although it is preferred that elastomeric ring of material 40 be constructed from a rubber material, any other type of commercially available elastomeric material having a relatively high coefficient of friction is also contemplated for use.

Figure 5:
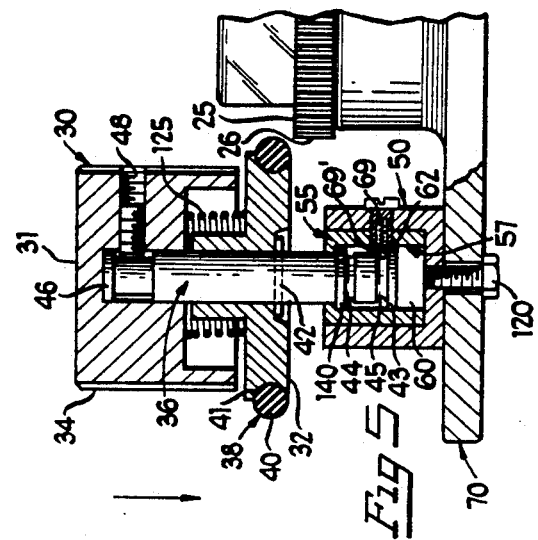
FIG. 5 of the drawings is an enlarged cross-sectional view of a portion of the ophthalmic dial advancement system showing, in particular, the lens rotation means including the rotation disengagement means, as attached to the barrier means, the shaft member of the lens rotation means, and, the disengaged positioning of the engagement means of the lens rotation means with respect to the outer engagement surface of the single dial sphere control of the ophthalmic refractor.

Shaft member 36 is shown in FIG. 4 and FIG. 5 as including shaft region 42, bottom end 43, upper portion 46 and grooves 44 and 45 formed proximate to the bottom end of the shaft. As shown in detail in FIGS. 4 and 5, upper portion 46 of shaft member 36 is operably positioned between top surface 31 and bottom surface 32 of lens rotation means 30 and secured therebetween by set screw 48 (although other types of conventional methods to secure the shaft in place, such as by a snap-fit or adhesive, are also contemplated for such securement). Shaft region 42 is operably positioned adjacent bottom surface of integrateable lens rotation means 30 and bottom end 43 is operably disposed within a portion of rotation disengagement means 50. As will be explained, grooves 44 and 45 cooperate with biased protrusion 62 (FIG. 5) so as to facilitate alternative positioning of lens rotation means 30 between an engaged position (FIG. 4), with respect to outer engagement surface 26 of single dial sphere control 25, and a disengaged position (FIG. 5).

Rotation disengagement means 50 is shown in FIG. 4 and FIG. 5 as being operably attached to barrier means 70 and shaft member 36 of lens rotation means 30. Rotation disengagement means 50 comprises engagement locking means 55 which includes retaining means 57 (FIG. 5). Retaining means 57 includes channel means 60 (FIG. 5) having a biased protrusion 62 depending from bore 68 (FIG. 4), wherein biased protrusion 62 is partially inserted within the channel means. Biased protrusion 62 comprises a spring 64 (FIG. 4) having a first end 65 and a second end 66, and a ball 67 (FIG. 4) operably attached to the second end of the spring. The spring is positioned within bore 68. Bore 68 is formed transverse to the longitudinal axis of channel means 60, and includes substantially closed end 69 and aperture 69' (FIG. 5). Accordingly, first end 65 of spring 64 abuts with closed end 69, and first end 65 of spring 64, and in turn ball 67, are operably positioned adjacent aperture 69'.

Channel means 60 accepts the grooved portion of shaft member 36, and, in cooperation with biased protrusion 62 releasably maintains lens rotation mean 30 in either an engaged position (FIG. 4) or a disengaged position (FIG. 5). Indeed, if a practitioner desires to advance single dial sphere control 25 via engagement with and through the more precise and sensitive lens rotation means 30, the practitioner would simply push the lens rotation means downward in the direction of the arrow (as shown in FIG. 5). As the integrateable lens rotation means is pushed down, ball 67 of protrusion 62 will be biased back toward closed end 69 of bore 68, and accordingly, the ball will become unseated from groove 44—thereby releasing shaft member 36, and, in turn, lens rotation means 30 from its maintained disengaged position. Furthermore, as bottom end 43 of shaft member 36 progresses substantially all the way into channel means 60, ball 67 will be biased into groove 44—thereby releasably maintaining integrateable lens rotation means 30, and more particularly, elastomeric ring of material 40 in operable engagement with engagement surface 26 of single dial sphere control 25 (FIG. 4). It should be noted that even when the lens rotation means is in the engaged position, a practitioner would not be precluded from alternative direct advancement of single dial sphere control 25 for purposes of advancing the lens power.

If the practitioner desires to disengage lens rotation means 30 from operable contact with engagement surface 26 of single dial sphere control 25, such disengagement can be achieved by simply pulling the lens rotation means upward in the direction of the arrow, as shown in FIG. 4, until the spring loaded ball is biased back into groove 45 (FIG. 5) Accordingly, once ball 67 has been properly seated within groove 45, elastomeric ring of material 40, and in turn engagement means 38 will no longer be in contact with single dial sphere control 25. Although biased protrusion 62 is shown as a spring loaded ball, other types of protrusions, such as non spring loaded, or rib members, are also contemplated for cooperation with the grooves of the shaft member so as to facilitate releaseable securement of the shaft in an engaged, or disengaged, position as the result of a snap fit therebetween. Also shown in FIGS. 4 and 5 are bolt 120 which secures rotation disengagement means 50 to barrier means 70, spring 125 and lip portion 140 which precludes over extension of shaft member 36 when disengaging lens rotation means.

Figure 3:
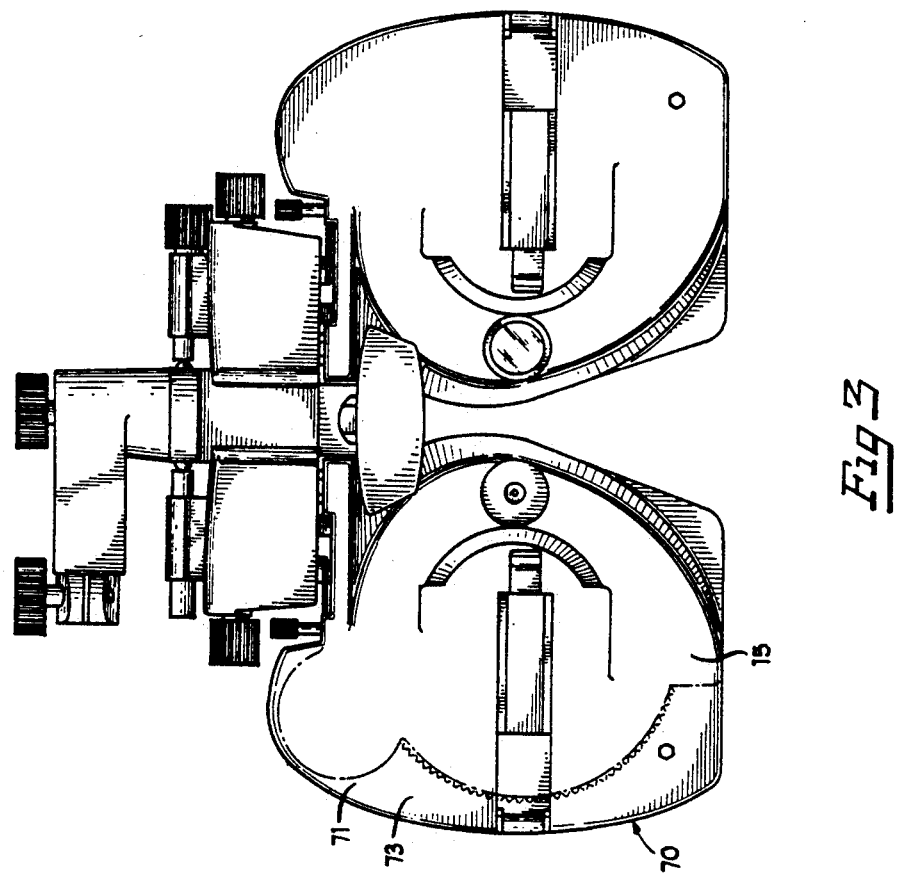
FIG. 3 of the drawings is an elevated back view of the ophthalmic dial advancement system as integrally attached to the lens housing means of the ophthalmic refractor, showing, in particular, the substantially planar positioning of the back surface of the barrier means with respect to the back side of the lens housing means of the ophthalmic refractor, as well as showing, the attachment means for securing the lens rotation means to the front panel of the barrier means.

Barrier means 70 is shown in FIGS. 1 through 3 as including extension piece 71 which is integrally formed to outer peripheral side edge 17 of housing means 12 (FIG. 2) and positioned adjacent back side 15 (FIG. 3) of the housing means. Barrier means 70 includes a front panel 72, a back panel 73 (FIG. 3), an inner edge 74 (FIG. 2) and an outer peripheral side panel 75 (FIG. 2). As shown in FIG. 1, front panel 72 is substantially parallel with front side 14 of housing means 12, and, back panel 73 (FIG. 2) is substantially planar with back side 15 of the housing means. As can be seen in FIG. 2, inner edge 74 is integrally attached adjacent outer peripheral side edge 17 of housing means 12, and outer peripheral side panel 75 of barrier means 70 is distally spaced from the inner edge so as to result in an outer peripheral surface. Inasmuch as the adjustment knobs and dials, and more particularly, the single dial sphere control 25 (FIGS. 2 and 3) are positioned adjacent to the practitioner during an eye examination, barrier means 70 actually serves to reduce inadvertent, and/or curiosity contact with the single dial sphere control 25 by the patient's hands by shielding exposure to same. In addition, barrier means 70 further provides the added benefit of serving as a guide surface for the practitioner's hand as he or she is advancing the single dial sphere control directly, or through the lens rotation means.

Figure 6:
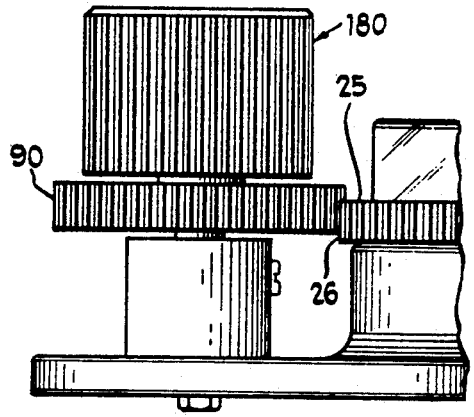
FIG. 6 of the drawings is an enlarged bottom view of the ophthalmic dial advancement system showing, in particular, the tooth-like surface of the engagement means of the lens rotation means in meshed engaged cooperation with the tooth-like surface of the outer engagement surface of the single dial sphere control.
Figure 7:
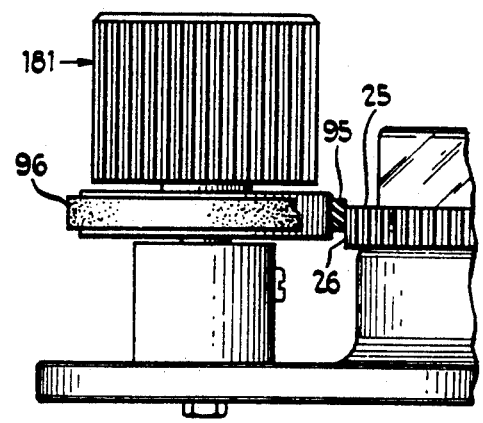
FIG. 7 of the drawings is a partial cross-sectional, enlarged bottom view of the ophthalmic dial advancement system showing, in particular, the frictional engagement between the elastomeric engagement means of the lens rotation means with the outer engagement surface of the single dial sphere control.

Two variations of engagement means for providing operable engagement with outer engagement surface 26 of single dial sphere control 25 are shown in FIG. 6 and FIG. 7. Engagement means 90 is shown in FIG. 6 as having a tooth-like surface which is in substantial alignment with the tooth-like surface of the engagement surface of the single dial sphere control. Accordingly, when the lens rotation means is positioned in its engaged orientation, such as shown in FIG. 4, the tooth-like surfaces will mesh together so as to facilitate advancement of the single dial sphere control upon turning of the lens rotation means.

Engagement means 95 is shown in FIG. 7 as comprising material 96, having a relatively high coefficient of friction applied to a portion of the outer surface of the lens rotation means. Accordingly, such material facilitates frictional engagement with the engagement surface of the single dial sphere control means when in the engaged position. Although material 96 is preferably constructed from rubber, any other type of commercially available material having a relatively high coefficient of friction is also contemplated for use. Also shown in FIG. 6 and FIG. 7 is the knurled surface 180 and 181, respectively, of a portion of the outer peripheral surface of the lens rotation means.

The foregoing description and drawings merely explain and illustrate the invention and the invention is not limited thereto except insofar as the appended claims are so limited as those skilled in the art who have the disclosure before them will be able to make modifications and variation therein without departing from the scope of the invention.

What is claimed is:

1. An ophthalmic dial advancement system comprising:

a vision testing apparatus having at least two symmetrically configured lens housing means for operably supporting one or more lenses, wherein each of said lens housing means include a front side and a back side, an outer peripheral side edge and a plurality of adjustment knobs and dials, including a weak sphere control dial having an outer engagement surface operably exposed adjacent to at least one of said front and back sides of each of said lens housing means, for advancing the lens power of at least one of the lenses in each of the lens housing means associated with said weak sphere control dial;

lens rotation means operably associated with at least one of said front side and said back side of said lens housing means in operably contact with said engagement surface of said weak sphere control dial for facilitating the alternative advancement of said weak sphere control dial upon turning of said lens rotation means, to in turn, provide increased manual sensitivity to a practitioner with respect to each increase or decrease in diopter steps associated with said weak sphere control dial during said advancement of said weak sphere control dial, to thereby preclude inadvertent under or over advancement of said lens power, said lens rotation means having a top surface, a bottom surface, an outer peripheral surface, and a shaft member having a top end operably attached at a position between said top and bottom surfaces of said lens rotation means and a bottom end operably attached to said lens housing means;

said lens rotation means further including engagement means operably positioned along at least a portion of one of said top surface, bottom surface and outer peripheral surface of said rotation means, for facilitating said operable contact, and, in turn, rotational advancement of said weak sphere contol dial upon turning of said lens rotation means by said practitioner, said engagement means operably contacting and engaging at least a portion of said outer engagement surface of said weak sphere control dial to impart rotation thereto, upon rotational advancement of said lens rotation means by a practitioner.

2. The invention according to claim 1 in which said engagement means comprises at least a portion of said outer peripheral surface of said lens rotation means having a configuration substantially engageable with said outer engagement surface of said weak sphere control dial for communicating rotation to said weak sphere control dial upon rotation of said lens rotation means.

3. An ophthalmic dial advancement system comprising:
   a vision testing apparatus having at least two symmetrically configured lens housing means wherein each of said lens housing means include a front side and a back side, an outer peripheral side edge and a plurality of adjustment knobs and dials, including a single dial sphere control having an outer engagement surface operably exposed adjacent to at least one of said front and back sides of each of said lens housing means, for advancing the lens power of at least one of the lenses in each of the lens housing means;
   lens rotation means operably associated with at least one of said front side and said back side of said lens housing means in operable contact with said engagement surface of said single dial sphere control for facilitating the alternative advancement of said single dial sphere control upon turning of said lens rotation means, to in turn, provide increased manual sensitivity to a practitioner during said advancement of said single dial sphere control, to thereby preclude inadvertent under or over advancement of said lens power.
   said lens rotation means having a top surface, a bottom surface, an outer peripheral surface, and a shaft member having a top end operably attached at a position between said top and bottom surfaces of said lens rotation means and a bottom end operably attached to said lens housing means;
   said lens rotation means further including engagement means operably positioned along at least a portion of one of said top surface, bottom surface and outer peripheral surface of said rotation means, for facilitating said operably contact, and, in turn, rotational advancement of said single dial sphere control upon turning of said lens rotation means by said practitioner,
   said engagement means operably contacting and engaging at least a portion of said outer engagement surface of said single dial sphere control to impart rotation thereto, upon rotational advancement of said lens rotation means by a practitioner;
   said ophthalmic dial advancement system further including rotation disengagement means operably attached to said lens rotation means for facilitating manipulatable positioning of said lens rotation means between a first engaged rotational position and a second disengaged rotational position, so as to alternatively engage and disengage rotational advancement of said single dial sphere control.

4. The invention according to claim 3 in which said rotation disengagement means further includes engagement locking means operably associated with at least a portion of said lens rotation means for releasably maintaining said lens rotation means in one of said first engaged rotational position and said second disengaged rotational position.

5. The invention according to claim 4 in which said engagement locking means comprises retaining means operably positioned within a portion of said lens housing means for releasable engagement with a portion of said shaft member proximate said bottom end of same.

6. The invention according to claim 5 in which said retaining means includes channel means for operably acceptance of a portion of said shaft member of said lens rotation means, said channel means including one or more protrusions operably positionable within a portion of said channel means,
   said shaft member having one or more grooves operably formed within said portion of said shaft member to be accepted within said channel means,
   said one or more grooves operably cooperating with said one or more protrusions for releasably securing said lens rotation means in one of said first engaged rotational position and said second disengaged rotational position.

7. The invention according to claim 6 in which said one or more protrusions include biasing means for insertion and release of said one or more protrusions within said one or more grooves of said shaft member during positioning of said lens rotation means from one of said first engaged rotational position and said second disengaged rotational position.

8. The invention according to claim 6 in which said shaft member is releasably secured within said channel means of said retaining means as the result of a snap-fit connection therebetween.

9. The invention according to claim 3 in which at least a portion of said rotation disengagement means is operably disposed between said bottom surface of said lens rotation means and said lens housing means.

10. An ophthalmic dial advancement system comprising:
    a vision testing apparatus having at least two symmetrically configured lens housing means wherein each of said lens housing means include a front side and a back side, an outer peripheral side edge and a plurality of adjustment knobs and dials, including a single dial sphere control having an outer engagement surface operably exposed adjacent to at least one of said front and back sides of each of said lens housing means, for advancing the lens power of at least one of the lenses in each of the lens housing means;
    lens rotation means operably associated with at least one of said front side and said back side of said lens housing means in operable contact with said engagement surface of said single dial sphere control for facilitating the alternative advancement of said single dial sphere control upon turning of said lens rotation means, to in turn, provide increased manual sensitivity to a practitioner during said advancement of said single dial sphere control, to thereby preclude inadvertent under or over advancement of said lens power,
    said lens rotation means having a top surface, a bottom surface, an outer peripheral surface, and a shaft member having a top end operably attached at a position between said top and bottom surfaces of said lens rotation means and a bottom end operably attached to said lens housing means;
    said lens rotation means further including engagement means operably positioned along at least a portion of one of said top surface, bottom surface and outer peripheral surface of said rotation means, for facilitating said operable contact, and, in turn, rotational advancement of said single dial sphere control upon turning of said lens rotation means by said practitioner,
    said engagement means operably contacting and engaging at least a portion of said outer engagement surface of said single dial sphere control to impart rotation thereto, upon rotational advancement of said lens rotation means by a practitioner;

said engagement means comprising means operably attached to at least a portion of said outer peripheral surface of said lens rotation means for providing frictional engagement with said outer engagement surface of said single dial sphere control upon rotation of said lens rotation means.

11. The invention according to claim 10 in which said engagement means comprises a substantially elastomeric ring operably positioned about the outer peripheral surface of said rotation means.

12. An ophthalmic dial advancement system comprising:

a vision testing apparatus having at least two symmetrically configured lens housing means wherein each of said lens housing means include a front side and aback side, an outer peripheral side edge and a plurality of adjustment knobs and dials, including a single dial sphere control having an outer engagement surface operably exposed adjacent to at least one of said front and back sides of each of said lens housing means, for advancing the lens power of at least one of the lenses in each of the lens housing means;

lens rotation means operably associated with at least one of said front side and said back side of said lens housing means in operable contact with said engagement surface of said single dial sphere control for facilitating the alternative advancement of said single dial sphere control upon turning of said lens rotation means, to in turn, provide increased manual sensitivity to a practitioner during said advancement of said single dial sphere control, to thereby preclude inadvertent under or over advancement of said lens power, said lens rotation means having a top surface, a bottom surface, an outer peripheral surface, and a shaft member having a top end operably attached at a position between said top and bottom surfaces of said lens rotation means and a bottom end operably attached to said lens housing means;

said lens rotation means further including engagement means operably positioned along at least a portion of one of said top surface, bottom surface and outer peripheral surface of said rotation means, for facilitating said operable contact, and, in turn, rotational advancement of said single dial sphere control upon turning of said lens rotation means by said practitioner, said engagement means operably contacting and engaging at least a portion of said outer engagement surface of said single dial sphere control to impart rotation thereto, upon rotational advancement of said lens rotation means by a practitioner;

said ophthalmic dial advancement system further including barrier means operably attached to a portion of each of said two symmetrical lens housing means for restricting a patient from hand contact with at least one of said plurality of adjustment knobs and dials on said lens housing means, as well as to facilitate guided manipulation of said rotation means and, said single dial sphere control by a practitioner, said barrier means having a front panel, a back panel, an outer peripheral side panel disposed between said front and back panel, and an inner edge panel opposing said outer peripheral side panel, wherein said inner edge panel is operably attached contiguously with at least a portion of said outer peripheral side edge of said lens housing means, said lens rotation means being operably attached to a portion of said barrier means.

13. The invention according to claim 12 in which said barrier means comprises extension pieces integrally formed with and juxtaposed to the said outer peripheral side edge of said lens housing means.

14. The invention according to claim 12 in which said ophthalmic dial advancement system further includes rotation disengagement means operably attached to said lens rotation means for facilitating manipulatable positioning of said lens rotation means between a first engaged rotational position and a second disengaged rotational position, so as to alternatively engage and disengage rotational advancement of said single dial sphere control as a function of rotation of said lens rotation means.

15. The invention according to claim 14 in which said rotational disengagement means further includes engagement locking means operably associated with at least a portion of said lens rotation means for releasably maintaining said lens rotation means in one of said first engaged rotational position and said second disengaged rotational position.

16. The invention according to claim 15 in which said engagement locking means comprises retaining means operably positioned within a portion of said barrier means for releasable engagement with a portion of said shaft member proximate said bottom end of same.

* * * * *

UNITED STATES PATENT AND TRADEMARK OFFICE
CERTIFICATE OF CORRECTION

PATENT NO. : 5,278,593
DATED : January 11, 1994
INVENTOR(S) : Ronald Roy Nielsen and Erwin Witt It is certified that error appears in the above-indentified patent and that said Letters Patent is hereby corrected as shown below:

| | |
|---|---|
| Col. 8 line 34 | Delete "operably" and insert instead -- operable --. |
| Col. 9 line 9 | Delete "aback" and insert instead -- a back --. |
| Col. 9 line 27 | After lens power delete "." and insert instead -- , --. |
| Col. 9 line 38 | Delete "operably" and insert instead -- operable --. |
| Col. 11 line 18 | Delete "aback" and insert instead -- a back --. |

Signed and Sealed this

Nineteenth Day of July, 1994

Attest:

BRUCE LEHMAN

Attesting Officer     Commissioner of Patents and Trademarks